United States Patent [19]

Muncheryan

[11] Patent Number: 4,808,789
[45] Date of Patent: Feb. 28, 1989

[54] DIODE-PUMPED-LASER INSTRUMENTATION SYSTEM

[76] Inventor: Hrand M. Muncheryan, 1735 Morningside, Orange, Calif. 92667

[21] Appl. No.: 10,817

[22] Filed: Feb. 4, 1987

[51] Int. Cl.$^4$ .............................................. B23K 26/00
[52] U.S. Cl. ........................ 219/121.6; 219/121.79; 219/121.75; 372/22
[58] Field of Search ............ 219/121.79, 121.68, 219/121.6, 121.85, 121.75; 372/75, 22

[56] References Cited

U.S. PATENT DOCUMENTS

| | | | |
|---|---|---|---|
| 3,383,491 | 5/1968 | Murcheryan | 219/121 LV X |
| 3,622,743 | 11/1971 | Murcheryan | 219/121 LH X |
| 3,735,280 | 5/1973 | Johnston, Jr. | 372/75 X |
| 3,947,780 | 3/1976 | Rice et al. | 372/22 X |
| 4,068,190 | 1/1978 | Ferguson | 372/22 X |

*Primary Examiner*—C. L. Albritton

[57] ABSTRACT

A semiconductor-diode-pumped solid-state laser instrumentation system for use in industrial materials processing, spectroscopy, medical surgery, metrology, fiberoptic communication, and related research work in a scientific laboratory is described. The system principally comprises a hand-held instrumentation stylus containing a laser-generating source consisting of a laser rod with an array of semiconductor radiation-emitting diodes disposed in adjacent relation to said laser rod for producing a high-quality and stable beam of laser radiation therefrom. The system is further capable of generating harmonic wavelengths of said radiation at Q-switched and modelocked formats.

17 Claims, 1 Drawing Sheet

DIODE-PUMPED-LASER INSTRUMENTATION SYSTEM

The present invention is generally related to a laser-generating system and is more particularly concerned with a system adapted to generate a high-quality laser beam by the use of a solid-state laser rod optionally pumped (excited to produce) by an array of laser diodes to generate a laser radiation and harmonic wavelengths thereof.

BACKGROUND OF THE INVENTION

This invention relates to an improved embodiment of a laser instrumentation device described and claimed by this applicant, in the U.S. Pat. No. 3,786,907, and an earlier patent related to the same instrumentation system, U.S. Pat. No. 3,464,534. Both of these patents describe and claim semiconductor diode lasers as sources of laser radiation. However, U.S. Pat. No. 3,786,907 specifically discloses and claims a semiconductor diode-pumped laser generator for application in various industrial processes, more particularly in a laser eraser for correction of type-written errors. However the main point in this application resides in the use of new techniques and elements for generating laser radiation using newly-developed semiconductor diodes, such as light-emitting diodes or laser diodes. Both of these diodes are capable of producing spectral wavelengths compatible with the solid-state laser rods. However. the laser diode possesses the property of higher intensity of radiation and is more efficient in irradiating any solid-state laser rod and producing therefrom a laser-beam radiation of high performance characteristics.

The present invention further improves on said device shown in U.S. Pat. No. 3,786,907, and demonstrates that by frequency-doubling or Q-switching the laser diode's radiation or by using both the frequency-doubling and the Q-switching techniques a laser radiation beam is produced which has improved spectral and optical characteristics.

Conventional laser-generating systems employ inert-gas arc lamps, known as flashlamps, tungsten-filament lamps, and the like to illuminate (pump) the solid-state laser rod to generate laser radiation therefrom. The most common source of continuous pumping of laser radiation from a laser rod, such as a neodymium-doped yttrium-aluminum-garnet host (Nd-YAG), is the tungsten-filament halogen lamp. Another optical-pump source is the krypton arc lamp. The pumping lamp emits a blackbody-type radiation, whose efficiency in pumping a laser radiation from the solid-state rod, such as a ruby rod or a Nd-YAG rod, is between 5 to 6 percent. The light intensity from such a lamp heats it to a very high temperature. Therefore, most of the energy produced by the lamp is dissipated as thermal energy, which contributes to the heating of the laser-generating system, reducing its efficiency of emission. Consequently, cooling of the laser-generating system is necessary, using a cumbersome equipment of compressed air or water circulating through the laser-generating head. The service life of the lamp is short, typically 300 to 400 hours. These characteristics of the pumping lamp make the laser system bulky and costly to produce.

The efficiency of laser production of such an optical pumping lamp is also very low. For instance, for each 1000 watts of input power to the pumping lamp only about 25 watts of laser power is typically produced. This is an efficiency of about 2 percent, which is considered satisfactory at present because of the lack of other commercial means to produce greater efficiency of laser production. Furthermore, since the laser rod is heated by the thermal energy dissipated from the pumping light source, the efficiency of laser production of the rod also decreases, and its output becomes about 0.5 percent that of input. Accordingly, the present solid-state laser production techniques are too wasteful in energy utilization. For this reason, the laser systems are too costly for employment in many technical communities.

While the applicant's patent, U.S. Pat. No. 3,786,907, represents a new and basic principle of laser generation, by the use of a laser diode to pump a laser rod, such as Nd-YAG, ruby. erbium-YAG, alexandrite, or the like, the present application contains the same basic principle with improved design of construction using new elements to enhance additional advantages and efficiency to the laser system. As a matter of fact, the present disclosure fortifies the original basic system of the applicant's invention by the use of state-of-the-art laser-producing elements, fewer parts, low-cost materials, compactness in size, and more efficient laser pumping semiconductor laser diodes.

A typical laser diode for pumping laser rods is gallium arsenide (GaAs), which emits typically at about 8000 angstroms, with its hybrid from gallium-aluminum-arsenide (GaAlAs) emitting at 7500 to 9050 angstroms, and indium-gallium-arsenic-phosphide (InGaAsP) emitting at 11,000 to 16,000 angstroms in the infrared. Any of these laser diodes and their derivatives, such as for one gallium-indium-aluminum-arsenide (GaInAlAs) can be utilized in the present species of the applicant's invention, since each of these diodes has specific advatages, as will be presently indicated by reference to the drawings.

In the present invention, an array of any selected type of the laser diodes referenced above can be used. The diode offers a conversion efficiency of 25 percent and over, in some cases. This means that a 10-watts of input power can produce about 2.5 watts of laser radiation from the laser rod. An additional advantage of the diode laser over the flashlamp (tungsten-arc lamp, for instance) is that the radiation from the diode can be collimated and focused on the laser rod axially, matching with the $TEM_{oo}$ mode operation of the rod. $TEM_{oo}$ operation is the fundamental performance format of a laser element and is derived from the phrase "transverse electromagnetic mode", which mode simulates a Gaussian operational format, a most efficient performance mode of the laser system.

Since the semiconductor laser diode pumping of the laser rod possesses high effiency of radiation, the thermal problems are alleviated and consequent cooling operations, as necessary in other types of optical pumping methods, are not necessary. Thus, the cost of construction and operation of the laser system is reduced. Thermal birefringence effects and possible thermal focusing problems are also eliminated in diode pumping. One of the most important characteristics of the laser diode is the capability of being modulated easily at high speeds with high amplitude stabilization that is imparted to the laser rod by the diode performance.

By focusing the diode array radiation with a converging lens on the optical aperture of an optical fiber, the high energy from the diode array can be transferred through the fiber cable to a remotely-located laser rod, such as that shown in FIG. 2 of the drawing of the invention. This type of laser embodiment can enhance the reduction in the size of the laserhead; furthermore, a heatsink can be applied to the laserhead to cool it when necessary. The system then can be made small and simple in construction. Q-switching modelocking, tuning, and frequency-doubling design problems also become simplified and less costly, as shown in the present drawings.

SUMMARY OF THE INVENTION

Having described the many advantages of the present invention over the existing types of solid-state laser systems, the specific and principal advantages of the present invention may be further defined as follows:

To achieve high performance of the present invention, the principal object of the invention resides in the incorporation of a state-of-the-art laser diodes as the optical pumping source for the solid-state laser rod to produce an easily-generated high-quality laser beam at considerably lower cost than similar laser rods included in the present laser systems of commerce.

A further object of the invention is to provide a laser system with a minimum of operative parts using inexpensive materials and reducing the cost of production considerably and furnishing a more stable radiation performance than that heretofore has been achieved.

A still further advantage of the invention resides in its capability of the laser radiation to be easily Q-switched to achieve high-power laser output at short pulses, such as for nanoseconds, which characteristic becomes extremely important for certain types of medical surgery, semiconductor circuit development work, and military applications.

Another advantage of the invention is the provision of a harmonic generator (frequency-multiplying device) in the system, such as doubling the frequency and shortening the wavelength for applications requiring visible-wavelength laser radiations, which can be produced when necessary without increasing the number of inherent components of the system.

A further object of the invention resides in the provision of a remotely located gaseous source which is used by transmitting the gas through a fibroptic conduit, peripherally to the fiberoptic cable within the conduit, to the operative site, when the laser operation requires the oxidation of the debris from the focus of the laser beam incident on the specimen under operation.

One other advantage of the present invention is the provision of a fiberoptic laser conduit which contains therein a tubular space peripherally to the fiberoptic cable therein. The conduit has a tubular airtight sheathing externally thereto for purposes of suction of debris from the site of a medical surgey, when the device is used in a medical treatment by a surgeon.

A further object of the invention is the provision of a thermoelectric cooling device located peripherally to the laser-generating elements for maintaining a constant temperature therein in order to achieve the normal laser-emitting environment in the diode laser arrays.

Other objects and advantages of the invention will become more apparent from the specification taken in conjunction with the accompanying drawings, in which.

DETAILED DESCRIPTION OF THE INVENTION

Figure 1:
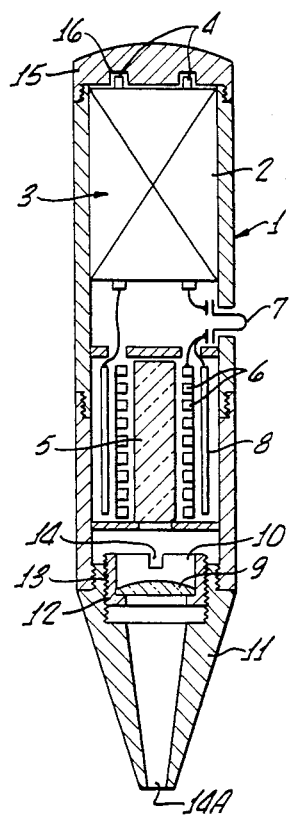
FIG. 1 is an axial, sectional view of the laser system showing the arrangement of the laser rod, laser diode arrays, the temperature-conditioning means, and the optical system to shape and direct the laser beam to the speciment to be worked thereupon.

Referring to the drawing in FIG. 1, numeral 1 points to the housing or stylus of the present invention with an outside container wall shown by the hatched structure that embodies the laser system and the optical elements that shape the emergent laser beam therefrom. Internally and at the uppermost part of the housing or stylus 1 is a chamber 2 containing a power-supply means or a rechargeable battery 3 with electric contacts 4 that can be plugged into a 115-volt electric source for charging the power supply source. Centrally to the device 1 is a laser rod 5 with a diode array 6 peripherally thereof. The laser rod may be one of several types of laser rods, such as Nd-YAG, Nd-glass, ruby, erbium-YAG, alexandrite, or the like. The peripherally located diode array 6 is used for producing a laser radiation when the switch 7 is closed for activation thereof by the power supply or battery 3. The radiation from the diode array 6 becomes incident on the laser rod 5, activating it to emission of a laser radiation therefrom.

In producing a high-intensity radiation from the laser diode array a quantity of thermal energy may be given off from the diode array 6. This heat is dissipated by means of the thermoelectric cooler 8 which is located in the periphery of the laser diode array 6 and is connected to the power supply 3 through the switch 7 and energized thereby. The thermoelectric cooler consists of a circuit having two electric junctions, one of which comprises dissimilar metals with their ends joined by welding together. When a direct current (such as from the battery) passes through this junction it becomes cold (the other junction is not used in this case).

the emitted laser radiation from the laser rod 5 is projected on an optical lens 9 located in a housing or receptacle 10 disposed the laser rod 5 and is movable up and down in the conical section 11 of the stylus. The receptacle 10 is provided on its periphery with screw threads 12 fitted into the internal threads 13 of the conical section 11, so that when the receptacle 10 is rotated by means of a screwdriver inserted into the slot or notch 14 and rotated clockwise or counterclockwise, the lens 9 is respectively positioned closer or remotely from the radiation exit port 14A through which the focused laser beam exits to the exterior to impinge on the workpiece. Numeral 15 is the cap member of the stylus 1 which has a circular groove 16 inferiorly thereof for accommodating the contacts 4 for transfering an external current into the rechargeable battery (or the power supply) 3 when inserted into a 115-volt current outlet.

Figure 2:
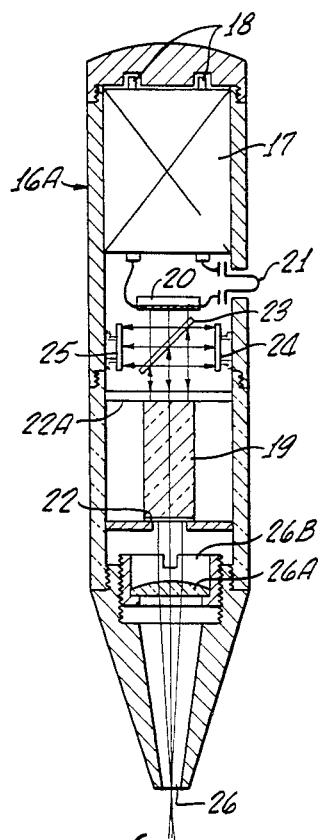
FIG. 2 is the sectional view of a second embodiment of the invention in which the optical pump radiation from the laser diode array is directed axially to the laser rod.

FIG. 2 represents another embodiment of the invention, in which the housing 16A contains, similar to that in FIG. 1, a rechargeable battery 17 with electrical contacts 18 for charging the battery 17 upon exhaustion thereof. Centrally to the housing 16A is a laser rod 19, of a material preferably Nd-YAG or Nd-glass or an erbium laser, which is optically pumped by a semiconductor laser-diode array 20 when the switch member 21 is depressed to make contact between the circuits of the diode array 20 and the battery means 17, which furnishes a direct current of proper amount to the diode array 20 to excite it to emission of a coherent radiation.

The emitted radiation from the diode array 20 is projected to the laser rod 19, as indicated by the arrows, to generate therein a laser radiation characteristic of the rod material. The laser rod 19 is partially coated with a reflective coating 22 at one end surface and contains no coating at its opposite end surface contiguous with the transparent partition means 22A. Accordingly, the laser beam from the diode array 20 impinges on the coating 22 and reflects therefrom to a semitransparent (dichroic) element 23, from which it reflects unto a mirror 24. The beam from the mirror 24 again reflects to mirror 25, by passing through the dichroic element 23 and back to mirror 24 and the coating 22. This process continues (within nanoseconds) to radiation saturation, whereupon the laser beam passes from the rod 19 through the coating 22 and impinges on the lens 26A, which projects the beam convergently to the exterior of the housing 16A through the tip or exit aperture 26. The lens 16A and its holder (receptacle) 26B have the respective functions as the lens 9 and its holder 10, shown in FIG. 1, in positioning the lens 26A up and down the conical section of housing 16A.

Figure 3:
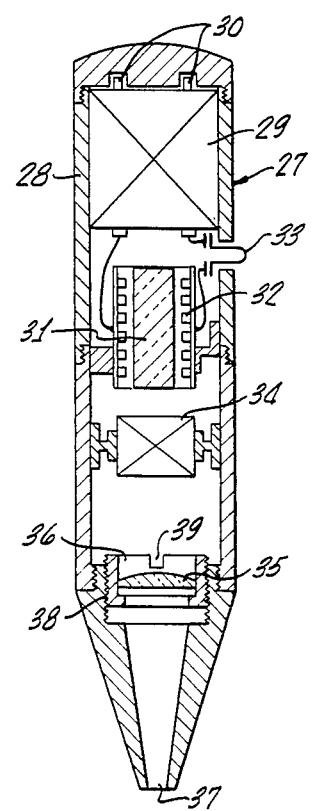
FIG. 3 is the sectional view of a third embodiment of the invention in which the radiation wavelength from a peripherally pumped laser rod is frequency-multiplied by a harmonic generator module located in the axial aspect of the laser system and in the path of the emergent laser beam from the laser stylus.

In FIG. 3 is another embodiment of the invention shown, in which the numeral 27 indicates a laser stylus (tubular housing) with housing 28 containing a rechargeable power supply or battery 29 which may be inserted by means of contacts 30 into the outlet socket of a 115-volt current to be recharged thereby. Centrally to the stylus 27 is a laser-generating solid-state rod 31 surrounded by a laser-diode array 32, which is electrically connected to the power supply 29 through a switch 33. When the switch 33 is pressed, it closes the power supply 29 circuit to the laser-diode array 32, activating it to emission of a laser radiation, which illuminates (pumps) the solid-state laser rod 31 and causes it to emit a high-intensity laser radiation characteristic of the rod material.

The emitted radiation from the laser rod 31 passes through a frequency-multiplying (harmonic generator) non-linear crystalline means 34, which increases the frequency of the radiation, preferably doubles it, and decreases the wavelength to one-half its fundamental wavelength. Assuming that the solid-state laser rod 31 is a Nd-YAG element, the fundamental radiation from it is 10,600 angstroms, and when a frequency-doubling occurs the wavelength becomes 5300 angstroms, which is in the visible spectral range. A frequency-doubled laser radiation possesses higher laser energy (energy=hf, where h is Planck's constant) and therefore can function as a higher-power laser radiation than when the radiation is in the fundamental 10,600 angstroms.

The laser beam (frequency doubled) projects through the stylus 27 and becomes incident on a focusing lens 35, which directs the focus of the laser beam through the radiation exit port 37 to the externally-positioned work site. Naturally, the laser rod 31 is coated 100 percent at its end adjacent the power supply 29 in the drawing and only partially at its opposite end adjacent the harmonic generator 34, so that laser action can take place in the rod by the oscillation of the laser radiation therein.

The lens 35 is mounted in a receptacle 36 having external screw threads 38 thereon. The receptacle 36 can be moved up and down by rotating it, respectively, counterclockwise and clockwise by the use of a screwdriver inserted into the slot 39. This action moves the focus of the laser beam to and from the exit port 37. The reason for moving the focus axially to the stylus 27 is that certain materials of industry, or tissues in medical surgery, require focused laser beam and others require defocused radiation for processing them. A focused beam gives the highest thermal energy and a defocused beam has low energy per square area and can be used for thin metallic materials or for surface treatment of organic tissues in medical work.

Figure 4:
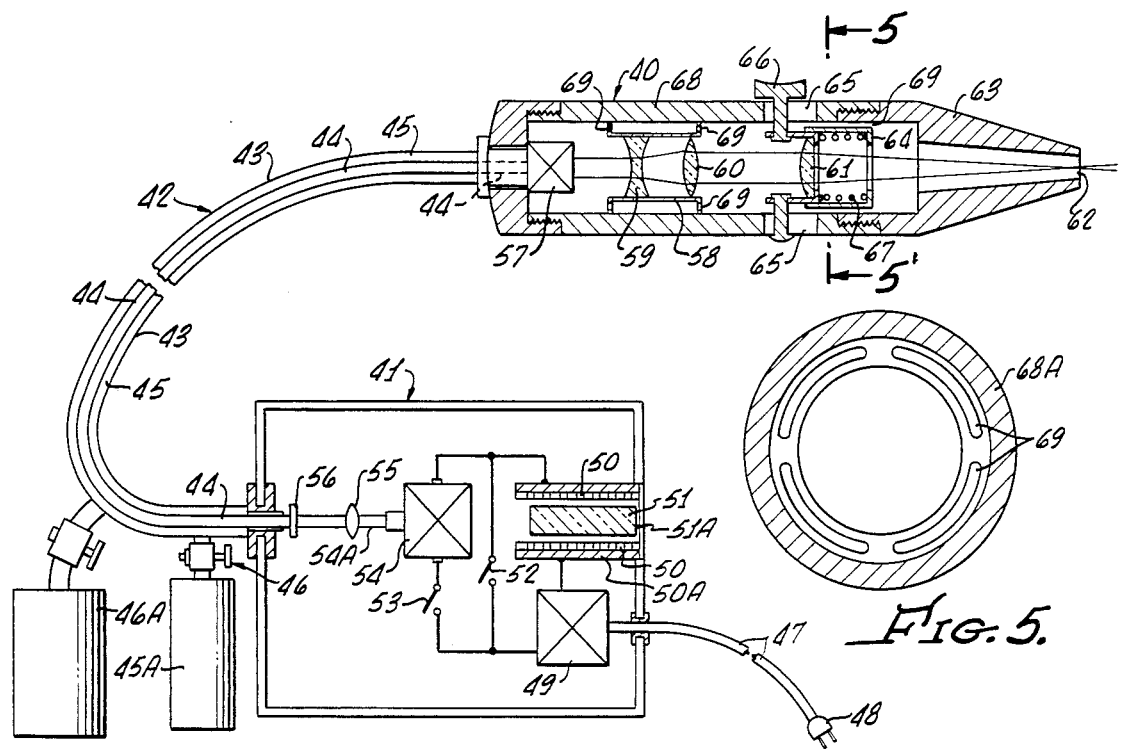
FIG. 4 represents a sectional view of another embodiment of the invention with the power supply, laser rod, its pumping and Q-switching modulae being contained in a housing remotely located from the laser wavelength-shaping and directing means connected to the laser source through a fiberoptic laser conduit.

FIG. 4 illustrates another embodiment of the invention, in which the stylus 40 receives the laser beam from the laser-generating section 41 through the fiberoptic conduit 42. The conduit 42 comprises a flexible external tubing 43, the fiberoptic bundle 44, and a peripheral tubular space 45 therebetween for transmitting a gas to the workpiece through the stylus 40, or it carries tissue debris by suction from the workpiece through the stylus 40, for operations involving medical surgery. The gas may be, for instance, pressurized oxygen contained in the tank 45A. The amount of gas issuing from the tank 45A is controlled by means of a valve 46. The suction apparatus is located in the container 46A.

Section 41 receives an alternating current from a 115-volt conventional electric outlet through the electric cord 47 having an electric plug 48 for insertion into the electric outlet socket. The alternating current is rectified and its intensity is controlled in the power-supply section 49, which may be conventional-type rectifier with control instruments. The controlled electric current from the power supply section 49 is transmitted to a laser-diode array 50 to energize it for producing an optical pumping radiation to activate the solid-state rod 51, such as Nd-YAG, to emission of radiation therefrom, when the switch 52 is closed. Surrounding the laser-generating rod 51 is an electric heat sink (thermal means) 50A, which is energized by a current from the power supply section 49, shown in drawing FIG. 4; this is used for cooling the laser-generating means. If both the switch 52 and switch 53 are closed, the Q-switching section 54 also become energized to increase the pulse power of the laser beam 54A from the rod 51 in the pulsing mode; this action shortens the pulse duration while at the same time retaining the laser pulse energy constant. When the laser rod 51 is operating in the continuouswave format, Q-switching provides shorter and more intense pulses than when the laser rod is pulsed by ordinary pulsing methods. The details of the power supply 49 and the Q-switch 54 are not given because they are commercially available as modules and are easily inserted into an electric circuit.

The Q-switched laser beam 54A passes through a lens 55 and the output mirror 56 to the fiberoptic line 42 to be transmitted to the stylus 40 for further optical processing therein. Since one surface 51A of the rod 51 is fully reflective by a mirror coating and the output mirror 56 is partially reflective the laser beam oscillates therebetween for stimulation and amplification before it exits through the mirror 56. After passing through the output mirror 56, the laser beam becomes continuous with the fiberoptic bundle 44, which conduits the laser beam into a harmonic generator 57 in the stylus 40. The position of the harmonic generator 57 may be shifted, if desired, so that the laser beam from the fiberoptic bundle 44 can continue its travel without optical transformation and impinges on the laser beam collimator 58. The collimator 58 collimates the laser beam and transmits it through the lens 60 to another lens 61, which focuses the laser beam upon the specimen or workpiece, as desired, positioned adjacent to the exit port 62 of the conical section 63.

The lens 61 is mounted in a circular receptacle 64 and can be moved up and down in the groove 65 by means of the button 66 attached to the receptacle 64. The receptacle 64 is biased by means of a spring 67, so that when the operator of the stylus desires to change the focus of the laser beam, he pushes on the button 66 to move the lens forward and thereby changes the focus position of the laser beam passing through the exit port 62. When it is desired to produce a Q-switched laser-beam output, the Q-switch section 57 is positioned in the beam path, as shown in the diagram of FIG. 4.

Figure 5:
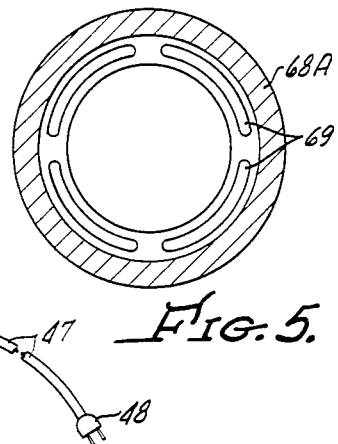
FIG. 5 is the cross-sectional view of the laser stylus taken on the line 4-4'.

FIG. 5 is a cross-sectional view of the stylus 40 taken in the line 4-4'. In the figure, the numeral 68A represents the cross-section of the wall 68 adjacent the groove 65. Numeral 69 indicates the slots through which the gaseous element from the tank 45A is transmitted to the exterior of the stylus through the radiation exit port 62.

In operation of any one of the species described, the respective power supply current is turned on by means of the respective switch in each embodiment of the invention. This action generates the laser radiation to be directed by the respective stylus, externally thereof, for applications described earlier in this specification. When the parts of any one of the stylus embodiments are to be changed or are to be repaired, the walls of the stylus housing are disassembled at the points of assembly, as shown in the diagrams, and then assembled after the replacement or repair has been undertaken.

I claim:

1. A semiconductor-diode-pumped-laser instrumentation system, comprising a housing means containing therein: a laser-generating means provided with a radiant semiconductor-diode means in contiguity thereof and disposed at one end of said housing means, an electric supply means in said housing means and connected to said radiant semicondutor-diode means to energize said diode means to produce a radiation therefrom for optically pumping said laser-generating means to emission of laser radiation, a thermal means disposed in adjacent relation to said laser-generating means and receiving an electric current from said electric supply means to temperature-condition said laser-generation means, a Q-switching means disposed on the path of said laser radiation emanating from said laser-generating means to produce an optical gain in said laser radiation, a radiant energy-conducting means connected to one end thereof to said Q-switching means for conducting a Q-switched laser radiation therefrom to a harmonic-wave-generating element connected at the other end thereof, with said harmonic-wave-generating element positioned in a radiation-receiving relation thereto for frequency-multiplying the laser-radiation beam received therefrom, a position-variable optical means disposed therein in the path of said laser-radiation beam projecting from said harmonic-wave-generating element for varying the intensity of said laser-radiation beam; said housing means being provided with a hollow, coniform section formed adjacent to said position-variable optical means to receive therefrom said laser-radiation beam and to direct it therethrough upon an object positioned externally thereto for laser-processing said object; and, means in said housing means to conduct a gaseous element therethrough to and from said object.

2. A semiconductor-diode-laser instrumentation system as defined in claim 1, wherein said laser-generating means is one of the solid-state lasing elements characterized by a laser rod of neodyminum-YAG, neodyminum-glass, erbium-YAG, ruby, and alexandrite.

3. A semiconductor-siode-pumped-laser instrumentation system as defined in claim 1, wherein said harmonic-wave-generating element is a nonlinear optical crystal selected from one of the phase-matched frequency-multipliers characterized by potassium pentaborate, potassium dihydrogen phosphate, potassium titanyl phosphate, and ammonium dihydrogen phosphate.

4. A semiconductor-diode-pumped-laser instrumentation system as defined in claim 1, wherein said radiant semiconductor-diode means is an array of semiconductor laser diodes positioned in the axial aspect of the laser-generating means consisting of a solid-state transparent rod capable of absorbing wavelengths compatible with the radiation emitted from said array of semiconductor-laser diodes and emanating a laser radiation.

5. A semiconductor-diode-pumped-laser instrumentation system as described in claim 1, wherein said electric supply means is an electric power source comprising a rechargeable electric battery having means to rectify the current from a 115-volt alternaring current source for recharging said battery.

6. A semiconductor diode-pumped-laser instrumentation system as defined in claim 1, wherein said electric supply means is a current source furnished by a current rectifier disposed therein to convert an alternating current received by said electric dupply means from an external alternating-current source, and a control means connected to said current rectifier to control the amount of current furnished by said electric supply means therein.

7. A semiconductor diode-pumped-laser instrumentation system as defined in claim 1, wherein said position-variable optical means comprises a receptacle with optical elements disposed therein for collimating the laser radiation beam received thereby from the harmonic-wave generating element therein; said receptacle having openings on its periphery to permit a gaseous element to pass therethrough peripherally thereof and through the hollow, coniform section to the exterior thereof.

8. A semiconductor diode-pumped-laser instrumentation system as defined in claim 1, wherein said radiant semiconductor-diode means is one of the category of semiconductor diode lasers characterized by gallium arsenide, gallium-aluminum-arsenide, gallium-aluminum-arsenic-phosphaide and their derivatives.

9. A semiconductor diode-pumped-laser instrumentation system as defined in claim 1, wherein said position-variable optical means has a spring-biased circular receptacle therearound with screw threads formed on the external periphery thereof, and a circular slot in the base of the hollow, coniform section having internal screw threads to accommodate therein said spring-biased circular receptacle having the optical means; said spring-biased circular receptacle is provided with two notches at the periphery thereof for accommodating a screwdriver point for rotating said receptacle within said internal screw threads and thereby to axially adjust the position of said optical means for focusing the laser beam transmitted therethrough to the exterior of said hollow, coniform section.

10. A laser instrumentation system as defined in claim 1, comprising a housing means containing therein a laser-generating means consisting of a solid-state optical rod of laser element with an illuminating semiconductor means disposed adjacent thereto to activate said solid-state optical rod of laser element to emission of laser radiation, a power supply means disposed in said housing to furnish current to said illuminating semiconductor means for energizing said illuminating semiconductor means to emission of a laser radiation which optically pumps said solid-state optical rod for radiation thereof, and a frequency-multiplying means positioned in adjacent relation to said laser-generating means in the path of a laser radiation therefrom to multiply the frequency thereof; said laser instrumentation system having a laser-beam-directing means comprising a hand-held stylus being optically connected to said housing means through a fiberoptic conduit having therein an optical fiber bundle extending from said laser-generating means to said hand-held stylus, a peripheral tubular chamber formed on the periphery of said fiberoptic conduit for conducting a gaseous element therethrough, a source of gaseous element connected to said fiberoptic conduit for transmission of the gaseous element into said fiberoptic conduit and into said hand-held stylus and therethrough to the exterior thereof; a suction means connected to the wall of said fiberoptic conduit for suction of effluents formed in adjacence to said hand-held stylus during the operation of said laser instrumentation system.

11. A laser instrumentation system, comprising a laser-generating means and a laser-dispensing means connected theretogether by means of a fiberoptic conduit with a fiberoptic bundle therein and an airspace disposed within said fiberoptic conduit peripherally thereof, a power supply means disposed in said laser instrumentation system to furnish a laser energization current to said laser-generating means to produce therefrom a laser radiation, a Q-switching means positioned adjacenetly to said laser-generatig means to receive said laser radiation therefrom and project it to one end of said fiberoptic conduit for transmission thereof to said laser-dispensing means through a harmonic-wave generator disposed therebetween, and a laser-radiation shaping means positioned adjacent to said harmonic-wave generator to receive the laser radiation therefrom and to collimate and project said laser radiation to the exterior of said laser-dispensing means; said laser-generating means having a chamber therein and a solid-state laser rod with a semiconductor diode array on the periphery thereof being disposed in said chamber and receiving a current from said power supply means to energize it to emission of a radiation, which illuminates said solid-state laser rod to produce a laser radiation therefrom and project it into said laser-dispensing means.

12. A laser instrumentation system as defined in claim 11, wherein said laser-dispensing means is provided therein with a frequency multiplying means positioned adjacent to the laser-radiation shaping means therein and in the path of the laser radiation passing therethrough for multiplying the pulse power of said laser radiation.

13. A semiconductor diode-pumped-laser instrumentation system as described in claim 1, having an enclosure containing therein a laser-radiation source, a semiconductor radiant means disposed in adjacent relation thereto, and an electric power source therein to energize said semiconductor radiant means to produce a radiation therefrom for illuminating said laser-radiation source for activation thereof to generate a laser radiation therefrom, and a thermal means surrounding said laser-radiation source and said semiconductor radiant means to temperature-condition and laser-radiation source and said semiconductor radiant means.

14. A laser instrumentation system comprising an enclosure means provided therein with a laser-generating section and a coniformended laser-dispensing section joined theretogether through a radiation-conducting means, said laser-generating section having a lasing rod with a semiconductor laser-pumping element positioned in contiguity thereof and a source of electric current to energize said semiconductor laser-pumping element for producing an illumination therefrom to activate said lasing rod to emission of a laser radiation, which being projected into said coniform-ended laser-dispensing section through said radiation-conducting means comprising a radiation-shaping means to collimate the radiation beam received from said laser-generating section and directing said radiation beam upon an object externally positioned to said coniformended laser-dispensing section for laser-processing said object.

15. A semiconductor diode-pumped-laser instrumentation system as defined in claim 1, wherein said thermal means in said housing means is a welded junction of two dissimilar metals which when supplied with an electric current from the electric supply means in said housing means produce a cooling effect therein to temperature-condition the laser-generating means located in said housing means.

16. In a semiconductor diode-pumped-laser instrumentation system comprising a tubular enclosure means with a chamber therethrough and having a source of laser radiation position at one end thereof, the opposite end of said tubular enclosure mens being coniform with an aperture therethrough, a radiation-wavelength-varying means disposed within said tubular enclosure means in the path of said laser radiation to vary the frequency thereof, and a position-variable optical means positioned in the base of said coniform end thereof to receive the frequency-varied laser radiation to project the radiation thereof convergently through the aperture of said coniform end to the exterior thereof.

17. A semiconductor-diode-pumped laser instrumentation system, having an enclosure means therefor, a lasing element provided with a semiconductor laser-exciting means in adjacence thereof being disposed therein, a power supply means in said enclosure means to furnish an electric current to said semiconductor laser-exciting means to energize said lasing element to emission of a laser radiation, a harmonic generator positioned in the path of the radiation projecting from said semiconductor lasing element through an optical-conducting medium disposed therebetween for incidence thereof upon an optical means for convergently projecting said laser radiation through a coniform section formed at one end of said enclosure means.

* * * * *